US012750222B2

(12) United States Patent
Horowitz et al.

(10) Patent No.: US 12,750,222 B2
(45) **Date of Patent: *Sep. 29, 2026**

(54) CHEMICAL SIGNATURE MANAGER

(71) Applicant: Wild Flower Holdings Inc., New York, NY (US)

(72) Inventors: Kari Horowitz, New York, NY (US); Neal Pomroy, Cos Cob, CT (US); David Wildenstein, Wellington, FL (US)

(73) Assignee: Wild Flower Holdings Inc., New York, NY (US)

( * ) Notice: Subject to any disclaimer, the term of this patent is extended or adjusted under 35 U.S.C. 154(b) by 1013 days.

This patent is subject to a terminal disclaimer.

(21) Appl. No.: 17/691,026

(22) Filed: Mar. 9, 2022

(65) Prior Publication Data

US 2023/0269081 A1 Aug. 24, 2023

Related U.S. Application Data

(63) Continuation-in-part of application No. 17/678,956, filed on Feb. 23, 2022, now Pat. No. 12,369,621, and (Continued)

(51) Int. Cl.

| | |
|---|---|
| ***H04L 9/32*** | (2006.01) |
| ***G06N 5/025*** | (2023.01) |
| ***G06Q 20/02*** | (2012.01) |
| ***G16C 20/20*** | (2019.01) |
| ***G16C 20/70*** | (2019.01) |
| *H04L 9/00* | (2022.01) |

(52) U.S. Cl.

CPC ........... *H04L 9/3213* (2013.01); *G06N 5/025* (2013.01); *G06Q 20/02* (2013.01); *G16C 20/20* (2019.02);

(Continued)

(58) Field of Classification Search

USPC ........................................................ 705/40

See application file for complete search history.

(56) References Cited

U.S. PATENT DOCUMENTS

| | | | |
|---|---|---|---|
| 9,155,337 | B2 | 10/2015 | Duncan |
| 10,206,888 | B2 | 2/2019 | Vu et al. |

(Continued)

OTHER PUBLICATIONS

U.S. Appl. No. 17/678,956, Non-Final Office Action mailed Dec. 17, 2024, 15 pages.

(Continued)

*Primary Examiner* — Jacob T Minskey

(74) *Attorney, Agent, or Firm* — Conley Rose, P.C.

(57) ABSTRACT

Methods, systems, and apparatus, including computer programs encoded on a computer storage medium, for managing chemical signatures are disclosed. In one aspect, a method includes the actions of receiving an original chemical signature, and an originating user identifier, the original chemical signature comprised of identifiers for one or more chemicals comprising a selected set of chemicals, and for each identified chemical at least a quantity of the selected set of chemicals. Responsive to the receiving of the original chemical signature, the actions further include generating an original hash based on at least a part of the original chemical signature and the originating user identifier. The actions further include storing on a distributed ledger the generated hash. Via at least one rule from a rules engine, the actions further include calculating an original attribution value associated with the originating user identifier.

20 Claims, 5 Drawing Sheets

Related U.S. Application Data a continuation-in-part of application No. 17/678,981, filed on Feb. 23, 2022, now abandoned, which is a continuation-in-part of application No. 17/678,956, filed on Feb. 23, 2022, now Pat. No. 12,369,621, application No. 17/691,026, filed on Mar. 9, 2022 is a continuation-in-part of application No. 17/683,181, filed on Feb. 28, 2022, now Pat. No. 12,280,999, which is a continuation-in-part of application No. 17/678,956, filed on Feb. 23, 2022, now Pat. No. 12,369,621.

(52) U.S. Cl.
CPC ............ *G16C 20/70* (2019.02); *H04L 9/3236* (2013.01); *G06Q 2220/00* (2013.01); *H04L 9/50* (2022.05); *H04L 2209/603* (2013.01)

(56) References Cited

U.S. PATENT DOCUMENTS

| | | | |
|---|---|---|---|
| 10,897,925 | B2 | 1/2021 | Pandolfino |
| 2009/0008407 | A1 | 1/2009 | Sevcik et al. |
| 2009/0069932 | A1 | 3/2009 | Rudick |
| 2015/0251891 | A1 | 9/2015 | Peters et al. |
| 2016/0368753 | A1 | 12/2016 | Bethuy et al. |
| 2018/0257306 | A1* | 9/2018 | Mattingly ............. B33Y 50/00 |
| 2020/0202409 | A1 | 6/2020 | Jikomes et al. |
| 2021/0307378 | A1 | 10/2021 | Rabie |
| 2021/0390531 | A1* | 12/2021 | Voorhees ............ G06Q 20/367 |
| 2021/0397758 | A1 | 12/2021 | Haeni et al. |

OTHER PUBLICATIONS

U.S. Appl. No. 17/683,181, Notice of Allowance mailed Dec. 18, 2024, 12 pages.
U.S. Appl. No. 17/683,181, Non-Final Office Action mailed Jun. 10, 2024, 9 pages.
U.S. Appl. No. 17/678,956, Restriction Requirement mailed Sep. 5, 2024, 6 pages.
U.S. Appl. No. 17/678,956, Notice of Allowance mailed Apr. 8, 2025, 8 pages.
U.S. Appl. No. 17/705,891, Office Action mailed Sep. 17, 2025, 21 pages.

* cited by examiner

CHEMICAL SIGNATURE MANAGER

CROSS-REFERENCE TO RELATED APPLICATION

This application is a continuation-in-part of U.S. application Ser. No. 17/678,956, filed Feb. 23, 2022; a continuation-in-part of U.S. application Ser. No. 17/678,981, filed Feb. 23, 2022, which is a continuation-in-part of U.S. application Ser. No. 17/678,956, filed Feb. 23, 2022; and a continuation-in-part of U.S. application Ser. No. 17/683,181, filed Feb. 28, 2022, which is a continuation-in-part of U.S. application Ser. No. 17/678,956, filed Feb. 23, 2022, all of which are incorporated by reference.

BACKGROUND

A common way to ingest substances is to smoke those substances, such as by burning a base substrate that contains one or more active ingredients by which the active ingredients are converted into an inhalant as "smoke," followed by the inhalation of the resulting smoke.

Presently, the use of inhalants via smoking is common for both medicinal and recreational use. For example, various blends of strains of grown *Cannabis* and related substances when smoked, are associated with experiences. Those experiences may include not only sensory effects such as taste and smell but also pharmacological effects. By way of another example, tobacco products are sometimes blended to deliver the desired set of sensory effects. However, such blends may be costly and/or difficult to obtain.

An arbitrary blend of substances can be characterized as a set of chemicals and their associated amounts. A need may arise to specify a known blend by such a set of chemical amounts, and subsequently to mechanically generate those chemicals using less costly and/or more readily available materials to closely match at least some of the experiences of the characterized arbitrary blend.

Distilled beverages that are sold commercially may be produced from plant materials. After a distillation process, each product may include distinct aromas and flavors, which can reflect raw materials that were used, method of distillation process performed, and/or post-distillation treatments made on the product. Flavor compounds in distilled beverages may be referred to as congeners. Different distilled beverages may have small differences in congener levels but have large differences in flavor and aroma intensities.

Presently, some are experimenting with different enhancements of distilled beverages, examples of which include aggregating raw materials of tobacco, alcohol, and similar products and then mechanically mixing the aggregated raw materials into the distilled beverages. These types of distilled beverages may be combined to come up with different flavors.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1:
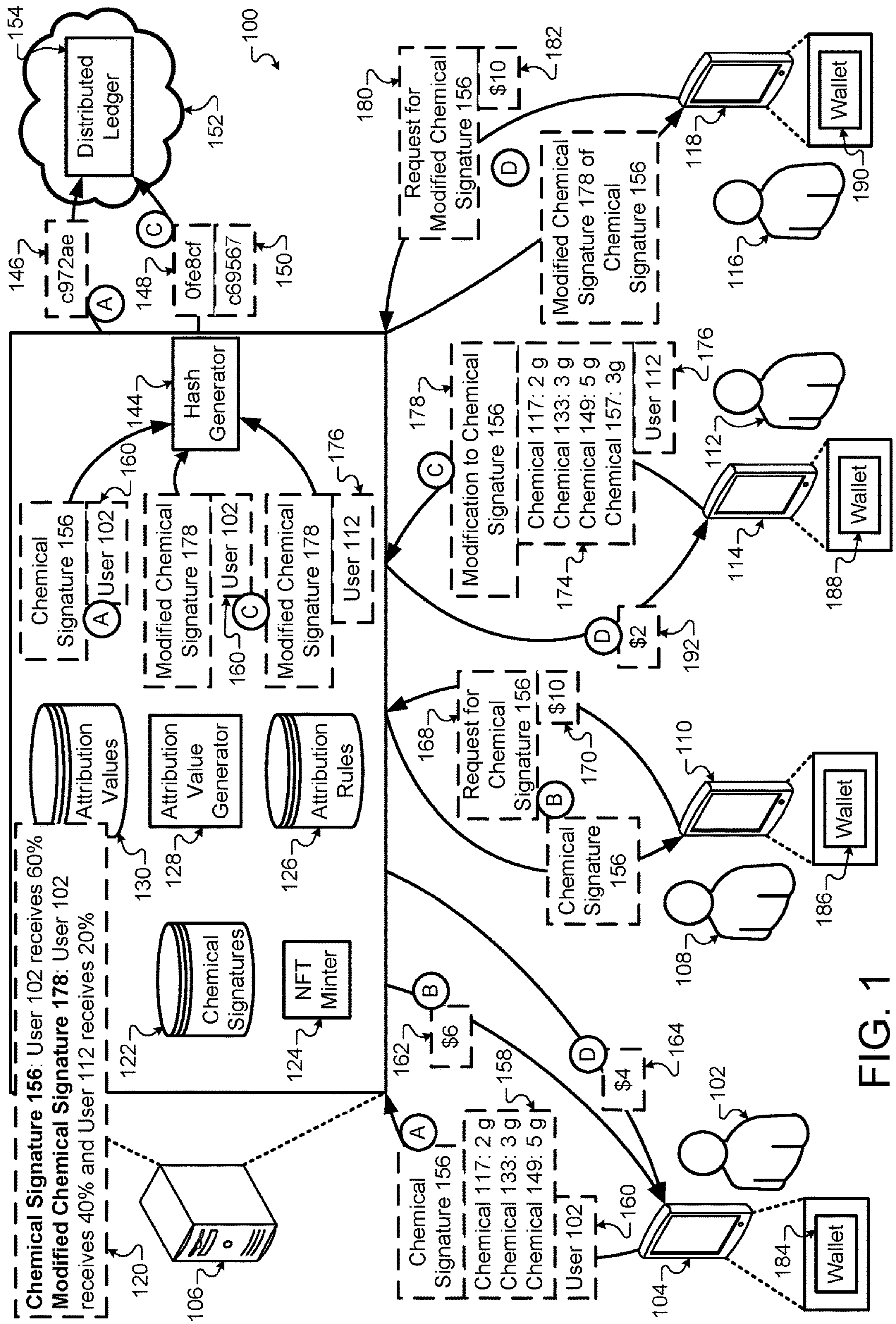
FIG. 1 is an example system that is configured to manage chemical signatures and determine compensation for creators of those chemical signatures.

This disclosure describes techniques for managing the customization of inhalants to improve a vaping or smoking experience. Particularly, the techniques may include receiving and sharing chemical signatures for inhalants or combustibles. The chemical signature may be related to a base flavor and a target flavor. The chemical signature may be received by the vaping or smoking apparatus from a server or another device. The base flavor may be associated with a wick that produces a flavor when heated or a combustible substrate that produces a flavorful smoke when lit. The produced flavor (or base flavor) may include, without limitation, tobacco, mint, mango, tropical fruit, cola, or other flavors, for example. The target flavor may include a combination of the base flavor and additional chemicals such as, without limitation, predetermined dosages of *Cannabis*, terpenes, or a suitable combination thereof. In one example, the vaping or smoking apparatus may utilize the chemical signature as a reference for injecting predetermined dosages of one or more pre-vapor formulations into a chamber of the vaping or smoking apparatus. The vaping or smoking apparatus may then apply heat to a combination of the base flavor and the pre-vapor or pre-smoke formulations in the chamber to generate the targeted flavor. Customizing inhalants may improve the vaping or smoking experience and reduce the cost of vaping or smoking by dynamically adjusting the amount of chemicals to be added to the base flavor depending on a target experience or flavor.

Without limitation, the chemical signature may include an information that identifies dosages, types, and/or other data associated with the chemicals to be used for generating a flavor change. The information may further identify a method, timing of injecting the pre-vapor or pre-smoke formulations to the chamber, and/or threshold values such as an airflow pressure threshold that can be used as a reference to activate a heating element in the vaping or smoking apparatus. In some implementations, the chemical signature is based upon a comparison between chemical components of the base flavor of the vaping or smoking apparatus and the selected target flavor. For example, the comparison may result in adding a particular dosage of cannabidiol or a terpene to a tobacco—base flavor during vaping or smoking. In this example, the additional particular dosage may be treated as a difference between the target flavor and the base flavor.

This disclosure describes techniques for managing the customization of beverages to improve the drinking experience. In some implementations, the beverage is a distilled beverage, although concepts described below may be applicable to other beverages. For example, the chemical signature of a beverage may be related to receiving a target flavor (e.g., from a selection of a target flavors received via a user interface) of a beverage dispenser, comparing chemical components of the target flavor with a base flavor. The chemical signature may also be related to a comparison between the target flavor and the base flavor. In some examples, the distilled beverage may include at least a liqueur. The chemical signature may be received by the beverage dispenser from a server or other device. In some examples, the base flavor may be associated with distilled beverages that include, without limitation, gin, tequila, vodka, whiskey, or rum. The target flavor may include a combination of the beverages and additional chemicals such as, without limitation, predetermined dosages of *Cannabis*, terpenes, or a suitable combination thereof. In one example, the beverage dispenser may utilize the chemical signature as a reference for injecting one or more formulations into a dispenser line that supplies the beverages from their corresponding kegs (or other container) to a beverage dispenser tower (or faucet). In this example, a mixture of the beverages and the formulations in the dispenser line may generate a combination that creates the selected or targeted flavor. Customizing beverages may improve the drinking experience and reduce the cost of drinking flavors by dynamically adjusting the amount of chemicals to be added to the base flavor as needed for an enhanced drinking experience.

Without limitation, the chemical signature may include information that identifies dosages, types, and/or other data associated with the formulations to be used for generating/creating the flavor or flavor change. The information may further identify a method or timing of injecting the formulations to the dispenser line. In one embodiment, the chemical signature can be based upon a comparison between chemical components of the base flavor and the selected flavor. For example, the comparison may result in adding a dosage of cannabidiol or a terpene to the distilled beverages. Here, the selected flavor may include additional dosages of cannabidiol, terpene, and/or tobacco.

As described herein, *Cannabis* is a genus of flowering plants that include the species: *Cannabis sativa, Cannabis indica*, and *Cannabis ruderalis. Cannabis* has long been used for hemp fibers, seed and seed oils, medicinal purposes, and recreational purposes. Cannabidiol, better known as "CBD," is one of the chemical compounds called "cannabinoids" that are found in the *Cannabis sativa* plant. The *Cannabis sativa* plant may also include terpenes, which are common compounds in the natural world. Terpenes are responsible for the smell of most plants. The terpenes may act on the endocannabinoid system in the human body in a similar way to the cannabinoids.

Details regarding the novel products and techniques referenced above and presented herein are described in detail, below, with respect to several figures that identify elements and operations used in systems, devices, methods, and computer-readable storage media that implement the techniques. Some embodiments are described of generating flavors for liqueurs or liqueur flavors. However, similar concepts may be applied to other beverages, distillates, and/or flavors, which are considered to be within the spirit and scope of the disclosure. Therefore, where the description refers to "flavors for liqueurs" or "liqueur flavors," the corresponding embodiments should be considered examples and not limited to liqueurs unless the context dictates otherwise.

FIG. 1 is an example system 100 that is configured to manage chemical signatures and determine compensation for creators of those chemical signatures. Briefly, and as described in more detail below, the system 100 includes a server 106 that receives various chemical signatures from users. The server 106 allows other users to access those chemical signatures. The server 106 may charge a fee to the users accessing the chemical signatures and provide compensation to the users who provided the chemical signatures. The server 106 may also allow users to modify existing chemical signatures. When other users access the modified chemical signatures, the server 106 may provide compensation to the originating user who provided the original chemical signature and the modifying user who modified the original chemical signature. The server 106 may also utilize a distributed ledger to manage the data related to the chemical signatures. FIG. 1 includes various stages A through D that may illustrate the performance of actions and/or the movement of data between various components of the system 100. The system 100 may perform these stages in any order.

In more detail, the user 102 may create a chemical signature 156. The chemical signature 156 may correspond to a formula 158. The formula 158 may specify two grams of chemical 117, three grams of chemical 133, and five grams of chemical 149. The chemical signature 156 may indicate a substrate to which the chemicals are added. The chemicals may be printed, injected, mixed, and/or any other combination method into the substrate. The chemical signature 156 may indicate a timing of the combining of the chemicals. The chemical signature 156 may correspond to a beverage to drink, a product to vape, a combustible material to smoke, and/or any other similar substance. The user 102 may use computing device 104 to communicate with the server 106. The user 102 may use the computing device 104 to transmit the chemical signature 156. The computing device 102 may also provide a user identifier 106 to the server 106. The computing device 102 and server 106 may be any type of computing devices that are configured to communicate with other computing devices. For example, the computing device 102 and/or the server 106 may be a desktop computer, laptop computer, mobile phone, smart watch, wearable device, and/or any other type of device that is configured to communicate with other devices. In some instances, the components of the computing device 102 and/or the server 106 may be distributed across multiple devices.

The computing device 104 may provide the chemical signature 156 and the user identifier 160 for the user 102 to the server 106. The server 106 may include a hash generator 144. The hash generator 144 may be implemented by one or more processors included in the server 106. The processors may execute code stored in a storage device included in and/or accessible by the server 106. The hash generator 144 may generate a hash 146 based on the chemical signature 156 and the user identifier 160 for the user 102. The hash generator 144 may store the hash 146 in distributed ledger 154. The distributed ledger 154 may use blockchain technology and may be accessible through a network 152. As an example, the hash generator may generate a hash 146 based on the chemical signature 156 and the user identifier 160 for the user 102. The hash 146 may be 0xc972ae. The server 106 may store the hash 146 in the distributed ledger 154. The server 106 may also store the chemical signature 156 and the user identifier 160 in the distributed ledger 154. In some implementations, the server 106 may store additional data in the distributed leger 154. In this case, the hash generator 154 may generate the hash 146 using that additional data including the chemical signature 156 and the user identifier 160.

The server 106 may include the chemical signatures storage 122. The chemical signatures storage 122 may be located in a storage device that is included in or accessible by the server 106. The chemical signatures storage 122 may store the various chemical signatures received from users. For example, the chemical signatures storage 122 may store the chemical signature 156. The chemical signature 156 may include the formula 158. The chemical signatures storage 122 may also store data identifying the originating user and/or a timestamp indicating the date and time that the server 106 received the chemical signature 156. In some implementations, the server 106 may store the chemical signature 156 and other chemical signatures in the distributed ledger 154. In the case of the chemical signature 156, the hash generator 154 may generate the hash 146 using the chemical signature 156, the user identifier 160, and the chemical signature 156.

The server 106 may include an attribution value generator 128. The attribution value generator 128 may be implemented by one or more processors included in the server 106. The processors may execute code stored in a storage device included in and/or accessible by the server 106. The attribution value generator 128 may be configured to determine an attribution value to assign to each of the chemical signatures received from users. The attribution value may indicate a percentage of a fee that an originating user receives when a requesting user pays the fee for the chemical signature provided by the originating user. Additionally, or alternatively, the attribution may indicate a fixed amount to pay the originating user when a requesting user pays a fee for the chemical signature provided by the originating user.

The attribution value generator 128 may generate an attribution value for a chemical signature using the attribution rules 126. The attribution rules 126 may specify what attribution value to assign to a chemical signature based on a variety of factors. Some of those factors may include the number of users who have requested the chemical signature, the period of time that the chemical signature has been included in the chemical signatures storage 122, the number of chemical signatures that the originating user has provided to the chemical signatures storage 122, the number of users who have requested the chemical signatures that the originating user has provided to the chemical signatures storage 122, the frequency that users have requested the chemical signatures that the originating user has provided to the chemical signatures storage 122, the attribution value of other chemical signatures that the originating user has provided to the chemical signatures storage 122, the attribution value of other chemical signatures in the chemical signatures storage 122, and/or any other similar factor. The factors may also be related to the formula 158 of the chemical signature 156. Some of these factors may include the attribution value of other chemical signatures that have one common ingredient, the attribution value of other chemical signatures that have two common ingredients, the attribution value of other chemical signatures that have three common ingredients, etc. Each of these factors may correspond to ranges and/or thresholds that may specify different attribution values.

In some implementations, the attribution value generator 128 may update the attribution value for a chemical signature. This may occur if a characteristic of the chemical signature changes and satisfies a new threshold and/or enters a new range. For example, an attribution rule may indicate that an originating user receives fifty percent of the fee from the requesting user if the number of users who have requested the chemical signature is less than thirty. The attribution rule may also indicate that an originating user receives sixty percent of the fee from the requesting user if the number of users who have requested the chemical signature is greater than thirty. Once the thirty-first user requests the chemical signature, then the attribution value generate may update the attribution value to sixty percent.

In some implementations, the attribution rules may be located in the distributed ledger 154 and stored as smart contracts. In this case, the smart contracts may include the various rules and/or thresholds of the attribution rules and may compare the corresponding characteristics of a chemical signature to determine the attribution value.

The attribution value generator 128 may store the attribution values in the attribution values storage 130. The attribution value generator 128 may store the attribution values in association with the chemical signatures and the originating user. For example, the attribution value generator 128 may determine the attribution value 120 for the chemical signature 156. The attribution value 120 may indicate that the user 102 should receive sixty percent of the fees received from the requesting user. In some implementations, the attribution values storage 130 may be included in the distributed ledger 154 and the attribution value generator 128 may communicate with the hash generator 144. In the case of the attribution value 120, the attribution value generator 128 provide the hash generator 144 the attribution value 120, the user identifier 160 of the user 102, and the attribution value of sixty percent. The hash generator 144 may calculate the hash for inclusion in the distributed ledger 154.

In the example of FIG. 1 and in stage A, the user 102 may use the computing device 104 to provide the chemical signature 156 to the server 106. The formula 158 for the chemical signature may specify two grams of chemical 117, three grams of chemical 133, and five grams of chemical 149. The server 106 may store the chemical signature 156 in the chemical signatures storage 122. The attribution value generator 128 may use the attribution rules 126 to determine the attribution value 120 for the chemical signature 156. The attribution value 120 may be that the user 102 receives sixty percent of the fee from the requesting user when the requesting user requests the chemical signature 156. The hash generator 144 may determine the hash 146 of the chemical signature 156 and the user identifier 134 of the user 102. The hash 146 may be 0xc972ae. The hash generator 144 may store the hash 146 in the distributed ledger 154.

The server 106 may allow the user 108 to request a chemical signature from the chemical signatures storage 122. The user 108 may use the computing device 110 to access the server 106. The computing device 110 may be a desktop computer, laptop computer, mobile phone, smart watch, wearable device, and/or any other type of device that is configured to communicate with other devices. The user 108 may use search queries to identify a desired chemical signature in the chemical signatures storage 122. The search queries may specify specific ingredients, specific techniques specified by the chemical signatures, originating users, modifying users, cost of the chemical signatures, submission date, number of users who have requested the chemical signatures, number of ingredients, chemical signature name, modified ingredients from an original chemical signature, brand of chemical signature, type of chemical signature (e.g., beverage, vaping, smoking, etc.), and/or any other similar characteristic of the chemical signatures. The server 106 may responds to the search queries with a list of chemical signatures that fit the search queries.

When the user 108 has identified a chemical signature to request, the user 108 may use the computing device 110 to request the identified chemical signature. The computing device 110 may transmit a request 168 that identifies the chemical signature. The computing device 110 may also transmit the request fee 170 that includes the fee for the requested chemical signature. The request fee 170 may be deducted from the wallet 186 of the user 108. The wallet 186 may be an electronic wallet that may access bank cards, cryptocurrency, peer to peer mobile payment service, and/or any other similar financial product. In some implementations, the balance of the wallet 186 may be included in the distributed ledger 154 and/or another distributed ledger.

In response to receiving the request 168 and the request fee 170, the server 106 may access the requested chemical signature and the attribution value that corresponds to the requested chemical signature from the attribution value storage 130. The server 106 may split the request fee 170 according to the attribution value for the requested chemical signature. The server 106 may provide the fee portion 162 to the originating user 102 identified in the attribution value in the attribution value storage 130 for the requested chemical signature. The computing device 104 may receive the fee portion 162 and store the fee portion 162 in the wallet 184 of the user 102. The wallet 184 may be an electronic wallet that may access bank cards, cryptocurrency, peer to peer mobile payment service, and/or any other similar financial product.

In the example of FIG. 1 and in stage B, the user 108 may use the computing device 110 to identify chemical signature 156. The user 108 may identify the chemical signature 156 by using various search queries. The server 106 may indicate that the fee for the chemical signature 156 is ten dollars. The user 108 may request the chemical signature 156 using the computing device 110. The computing device 110 may provide the request 168 to the server 106. The request 168 may indicate a request for the chemical signature 156. The computing device 110 may also provide the request fee 170 of ten dollars that is withdrawn from the wallet 186. The server 106 may receive the request 168 and the request fee 170. The server 106 accesses the chemical signature 156 from the chemical signatures storage 122. The server 106 provide the chemical signature 156 to the computing device 110. The server 106 identifies the attribution value 120 stored in the attribution values storage 130 for the chemical signature 156. The attribution rule 120 may indicate to provide the originating user 102 with sixty percent of the request fee 170. In this case, the server 106 may provide the computing device 104 of the user 102 with the fee portion 162 of six dollars that is sixty percent of the ten dollar request fee 170. The computing device 104 may store the fee portion 162 in the wallet 184 of the user 102.

The server 106 may provide users the ability to modify existing chemical signatures. In this case, a modifying user 112 may identify a chemical signature 156 to modify. The modifying user 112 may use the computing device 114 to identify a chemical signature 156 to modify. The computing device 114 may be a desktop computer, laptop computer, mobile phone, smart watch, wearable device, and/or any other type of device that is configured to communicate with other devices. The modifying user 112 may use various search queries to identify the chemical signature 156 similar to the user 108. The modifying user 112 may provide the formula 174 for the modification 172 to the chemical signature 156 to the server 106. This process may be similar to the user 102 providing the chemical signature 156 of the formula 158. In this way, the computing device 114 may provide the modification 172 to the chemical signature 156 with the formula 174 and the user identifier 176 for the user 112.

The server 106 may receive the modification 172 to the chemical signature 156 and the user identifier 176. The attribution value generator 128 may determine an attribution value 120 for the modifying user 112 and the originating user 102. The attribution value generator 128 may access the attribution rules 126 to determine the attribution value 120. The attribution rules 126 may include rules that indicate how to determine the attribution value 120 for more than one user in the case of the chemical signature being created by more than one user. Some of these rules may use the attribution value of the unmodified chemical signature or the previous version of the chemical signature, which may be the case for a chemical signature that is modified more than one time. Some of the factors that the attribution rules 126 may consider the number of users who have requested the chemical signature 156 and/or the modified chemical signature 178 of the chemical signature 156, the period of time that the chemical signature 156 and/or the modified chemical signature 178 of the chemical signature 156 has been included in the chemical signatures storage 122, the number of chemical signatures that the originating user and/or the modifying user has provided and/or modified, the number of users who have requested the chemical signatures or the modified chemical signatures that the originating user and/or the modifying user has provided and/or modified, the frequency that users have requested the chemical signatures that the originating user and/or the modifying user has provided and/or modified, the attribution value of the original chemical signature, the attribution value of the other chemical signatures that the originating user and/or the modifying user has provided and/or modified, the attribution value of other original and modified chemical signatures in the chemical signatures storage 122, and/or any other similar factor The factors may be related to the formula 174 of the modified chemical signature 178. Some of these factors may include the attribution value of other chemical signatures that have one common ingredient, the attribution value of other chemical signatures that have two common ingredients, the attribution value of other chemical signatures that have three common ingredients, etc. Each of these factors may correspond to ranges and/or thresholds that may specify different attribution values. The factors may also be related to the difference between the modified chemical signature 178 and the unmodified chemical signature 156. Some of these factors may include the number of common ingredients between the modified chemical signature 178 and the unmodified chemical signature 156, the amounts of those common ingredients, the common procedures specified in the modified chemical signature 178 and the unmodified chemical signature 156, the attribution values of other modifications to the original chemical signature, and/or any other similar factor.

The hash generator 144 may determine one or more additional hashes in response to receiving the modification to the chemical signature 156. The number of hashes may be related to the number of modifications that the server 106 has received to the original chemical signature. For example, if the original chemical signature 156 has been modified two sequential times (e.g., a modification to a modification), then the hash generator 144 may generate three hashes. Each hash may be based on the user identifiers of the modifying users and the modified chemical signature. The hash generator 144 may store the hashes 148 and 150 in the distributed ledger 154.

In the example of FIG. 1 and in stage C, the modifying user 112 may use the computing device 114 to communicate with the server 106. The modifying user 112 may identify the chemical signature 156 as one that the modifying user 112 wishes to modify. The modifying user 112 may identify the chemical signature 156 by using a search query, browsing a list of chemical signatures, following recommendations of other users, and/or any other similar search technique. The modifying user 112 may view the chemical signature 156 and modify it by adding three grams of the chemical 157.

The computing device 112 may provide the modified chemical signature 178 of the chemical signature 156 to the server 106. The computing device 112 may also provide the formula 174 that includes the formula of the modified chemical signature 178, which is two grams of chemical 117, three grams of chemical 133, five grams of chemical 149, and three grams of chemical 157. The computing device 112 may also provide the user identifier 176 of the user 112. The server 106 may store the modified chemical signature 178 in the chemical signatures storage 122.

The attribution value generator 128 utilizes the attribution rules 126 to determine the attribution value 120. The attribution value generator 128 may identify the original chemical signature 156 of the modified chemical signature 178 and determine that the user 102 is the originating user of the original chemical signature 156. The attribution value generator 128 may determine an attribution value 120 for the originating user 102 and for the modifying user 112. Based on the attribution rules 126, the attribution value generator 128 may determine that the originating user 102 receives forty percent of the fee from the requesting user and the modifying user 112 receives twenty percent of the fee from the requesting user.

The hash generator 144 may generate two new hashes to store in the distributed ledger 154. The first hash 148 may be the hash of the modified chemical signature 178 and the user identifier 160 of user 102. The hash generator 144 may calculate the hash 148 to be 0x0fe8cf. The second hash may be the hash of the modified chemical signature 178 and the user identifier 176 of the user 112. The hash generator 144 may calculate the hash 148 to be 0xc69567. The hash generator 144 may store both the hash 148 and the hash 150 in the distributed ledger.

Similar to the user 108 requesting the chemical signature 156, the server 106 may allow users to request modified chemical signatures from the chemical signatures storage 122. The user 116 may use the computing device 118 to access the server 106. The computing device 118 may be a desktop computer, laptop computer, mobile phone, smart watch, wearable device, and/or any other type of device that is configured to communicate with other devices. The user 112 may use search queries to identify a desired chemical signature in the chemical signatures storage 122 including those chemical signatures that are modified versions of other chemical signatures. The search queries may specify specific ingredients, specific techniques specified by the chemical signatures, originating users, cost of the chemical signatures, submission date, number of users who have requested the chemical signatures, number of ingredients, and/or any other similar characteristic of the chemical signatures.

When the user 116 has identified a chemical signature to request, the user 116 may use the computing device 118 to request the identified chemical signature. The computing device 118 may transmit a request 180 that identifies the chemical signature. The computing device 118 may also transmit the request fee 182 that includes the fee for the requested chemical signature. The request fee 182 may be deducted from the wallet 190 of the user 116. The wallet 190 may be an electronic wallet that may access bank cards, cryptocurrency, peer to peer mobile payment service, and/or any other similar financial product. In some implementations, the balance of the wallet 190 may be included in the distributed ledger 154 and/or another distributed ledger.

In response to receiving the request 180 and the request fee 182, the server 106 may access the requested chemical signature and the attribution value that corresponds to the requested chemical signature from the attribution value storage 130. The server 106 may split the request fee 182 according to the attribution value for the requested chemical signature. The server 106 may provide the fee portion 164 to the originating user 102 identified in the attribution value in the attribution value storage 130 for the requested chemical signature and the fee portion 192 to the modifying user 112 identified in the attribution value. The computing device 104 may receive the fee portion 164 and store the fee portion 164 in the wallet 184 of the user 102. The computing device 114 may receive the fee portion 192 and store the fee portion 192 in the wallet 188 of the user 112. The wallet 188 may be an electronic wallet that may access bank cards, cryptocurrency, peer to peer mobile payment service, and/or any other similar financial product.

In the example of FIG. 1 and in stage D, the user 116 may use the computing device 118 to identify the modified chemical signature 178. The user 116 may identify the modified chemical signature 178 by using various search queries. The server 106 may indicate that the fee for the modified chemical signature 178 is ten dollars. The user 116 may request the modified chemical signature 178 using the computing device 118. The computing device 118 may provide the request 180 to the server 106. The request 180 may indicate a request for the modified chemical signature 178. The computing device 110 may also provide the request fee 170 of ten dollars that is withdrawn from the wallet 190. The server 106 may receive the request 180 and the request fee 182. The server 106 accesses the modified chemical signature 178 from the chemical signatures storage 122. The server 106 provides the modified chemical signature 178 to the computing device 118. The server 106 identifies the attribution value 120 stored in the attribution values storage 130 for the modified chemical signature 178. The attribution rule 120 may indicate to provide the originating user 102 with forty percent of the request fee 182 and the modifying user 112 with twenty percent of the request fee 182. In this case, the server 106 may provide the computing device 104 of the user 102 with the fee portion 164 of four dollars that is forty percent of the ten dollar request fee 182. The computing device 104 may store the fee portion 164 in the wallet 184 of the user 102. The server 106 may provide the computing device 114 of the user 112 with the fee portion 192 of two dollars that is twenty percent of the ten dollar request fee 182. The computing device 114 may store the fee portion 192 in the wallet 188 of the user 112.

In some implementations, the server 106 may include a non-fungible token (NFT) minter 124. The NFT minter 124 may be configured to mint an NFT as part of hash generator 144 storing the hashes 146, 148, and 150 in the distributed ledger 154. The NFT minter 124 may store the NFTs in the distributed ledger 154. The NFT minter 124 may mint an NFT for the chemical signature and identify a corresponding user or users who created and/or modified the chemical signature. The NFT minter 124 may mint an NFT for each user who originated and modified the chemical signature. For example, the NFT minter 124 may mint two NFTs for the modified chemical signature 178 because two users created the modified chemical signature 178, the originating user 102 and the modifying user 112. The NFT minter 124 may mint an NFT for each chemical signature independent of the number of users who originated and modified the chemical signature. For example, the NFT minter 124 may mint one NFT for the modified chemical signature 178 independent of two users creating the modified chemical signature 178.

As part of the NFT minting process, the NFT 124 may indicate that the user who created and/or modified the corresponding chemical signature is the owner of the NFT. In this case, the NFT minter 124 may transfer ownership of the NFT in the case of a purchase of the chemical signature by another user. The selling owner may be compensated for the chemical signature according to the attribution values related to the chemical signature in question. For example, the NFT minter 124 may mint an NFT for the chemical signature 156. The originating user 102 may be the owner of the NFT of the chemical signature 156. The NFT minter 124 may transfer ownership of the NFT of the chemical signature 156 as part of the request for the chemical signature 156 from the user 108. For chemical signatures with originating users and one or more modifying users, the NFT minter may mint a single NFT for the modified chemical signature 178 or separate NFTs for each originating user and the one or more modifying users. In this case, the NFT minter 124 may transfer ownership of the NFT for the modified chemical signature 178 in response to a request for the modified chemical signature 178 from a requesting user. For multiple NFTs for a modified chemical signature 178 each owner user can transfer ownership according to the rules set forth by the respective owner.

Figure 2:
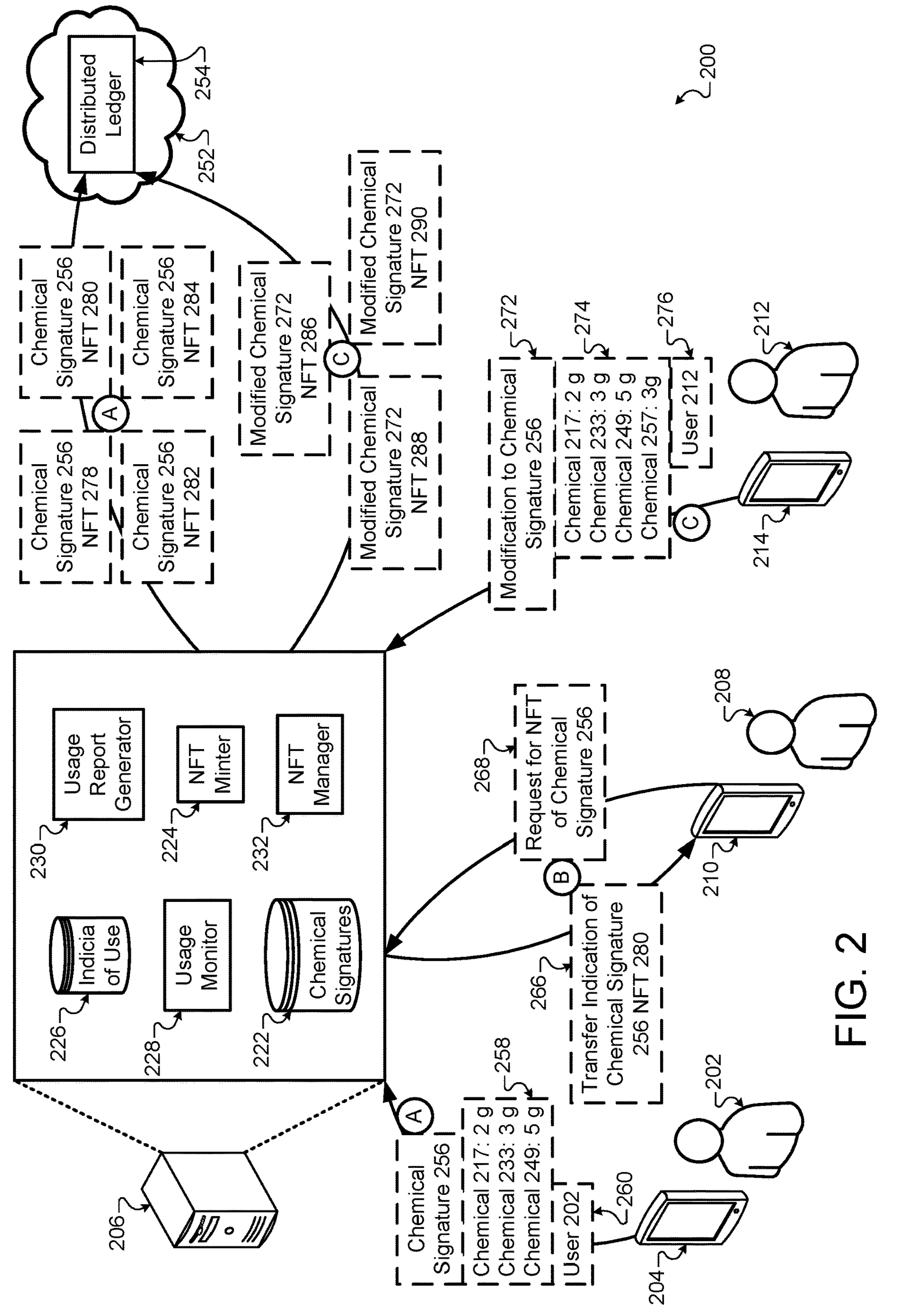
FIG. 2 is an example system that is configured to manage usage of chemical signatures using non-fungible tokens.

FIG. 2 is an example system that is configured to manage usage of chemical signatures using non-fungible tokens. Briefly, and as described in more detail below, the system 200 includes a server 206 that receives various chemical signatures from users. The server 206 allows other users to access those chemical signatures by using NFTs for each of the chemical signatures. The server 206 may also allow users to modify existing chemical signatures. When other users access the modified chemical signatures, the server 206 may provide generate additional NFTs. The server 206 may utilize a distributed ledger to manage the NFTs. FIG. 2 includes various stages A through C that may illustrate the performance of actions and/or the movement of data between various components of the system 200. The system 200 may perform these stages in any order.

In more detail, the user 202 may create a chemical signature 256. The chemical signature 256 may correspond to a formula 258. The formula 258 may specify two grams of chemical 217, three grams of chemical 233, and five grams of chemical 249. The user 202 may use computing device 204 to communicate with the server 206. The user 202 may use the computing device 204 to transmit the chemical signature 256. The computing device 202 may also provide a user identifier 206 to the server 206. The computing device 202 and server 206 may be any type of computing devices that are configured to communicate with other computing devices. For example, the computing device 202 and/or the server 206 may be a desktop computer, laptop computer, mobile phone, smart watch, wearable device, and/or any other type of device that is configured to communicate with other devices. In some instances, the components of the computing device 202 and/or the server 206 may be distributed across multiple devices.

The computing device 204 may provide the chemical signature 256 and the user identifier 260 for the user 202 to the server 206. The server 206 may include an NFT minter 224. The NFT minter 224 may be implemented by one or more processors included in the server 206. The processors may execute code stored in a storage device included in and/or accessible by the server 206. The NFT minter 224 may be configured to mint one or more NFTs that encapsulate a right to use the chemical signature 256. The NFT minter 224 may mint a limited number of NFTs for the chemical signature 256. The number of minted NFTs may be based on various rules that utilize factors similar to those used by the attribution rules 126 of FIG. 1. In some implementations, the NFT minter 224 receive the NFTs from a different device. In this case, the NFT minter 224 may identify the NFTs and associate them with the chemical signature 256.

The server 106 may store the NFTs in the distributed ledger 254. The distributed ledger 254 may use blockchain technology and may be accessible through a network 252. As an example, the NFT minter 224 may mint an NFT 278 based on the chemical signature 256. The NFT 278 may indicate that the user 202 has a right to use the chemical signature 256. The NFT minter 224 may store the NFT 278 and other NFTs in the distributed ledger 254.

The server 206 may include the chemical signatures storage 222. The chemical signatures storage 222 may be located in a storage device that is included in or accessible by the server 206. The chemical signatures storage 222 may store the various chemical signatures received from users. For example, the chemical signatures storage 222 may store the chemical signature 256. The chemical signature 256 may include the formula 258. The chemical signatures storage 222 may also store data identifying the originating user and/or a timestamp indicating the date and time that the server 206 received the chemical signature 256. In some implementations, the server 206 may store the chemical signature 256 and other chemical signatures in the distributed ledger 254.

In the example of FIG. 2 and in stage A, the user 202 may use the computing device 204 to provide the chemical signature 256 to the server 206. The formula 258 for the chemical signature may specify two grams of chemical 217, three grams of chemical 233, and five grams of chemical 249. The server 206 may store the chemical signature 256 in the chemical signatures storage 222. The NFT minter 224 may determine to mint four NFTs based on the chemical signature 256. The NFT minter 224 may determine to mint four NFTs based on various rules, such as the NFT minter 224 should mint four NFTs for a chemical signature that originates from a user who has not yet provided a chemical signature. The NFT minter 224 may store the four NFTs, NFT 278, 280, 282, and 284 in the distributed ledger 254. Initially, each of the NFTs 278, 280, 282, and 284 may indicate that the user 202 has the right to use the chemical signature 256.

The server 206 may allow the user 208 to request a chemical signature and/or the right to use a chemical signature in the chemical signatures storage 222. The user 208 may use the computing device 210 to access the server 206. The computing device 210 may be a desktop computer, laptop computer, mobile phone, smart watch, wearable device, and/or any other type of device that is configured to communicate with other devices. The user 208 may use search queries to identify a desired chemical signature in the chemical signatures storage 222. The search queries may specify specific ingredients, specific techniques specified by the chemical signatures, originating users, cost of the chemical signatures, submission date, number of users who have requested the chemical signatures, number of ingredients, and/or any other similar characteristic of the chemical signatures.

When the user 208 has identified a chemical signature to request, the user 208 may use the computing device 210 to request an NFT of the identified chemical signature. The computing device 210 may transmit a request 268 that identifies the chemical signature. In some implementations, the computing device 210 may also transmit a request fee that includes the fee for the NFT of the requested chemical signature. The request fee may be deducted from a digital wallet of the user 208. The wallet may be an electronic wallet that may access bank cards, cryptocurrency, peer to peer mobile payment service, and/or any other similar financial product. In some implementations, the balance of the wallet may be included in the distributed ledger 254 and/or another distributed ledger.

The server 206 may include an NFT manager 232. The NFT manager 232 may be implemented by one or more processors included in the server 206. The processors may execute code stored in a storage device included in and/or accessible by the server 206. The NFT manager 232 may be configured to process requests for NFTs, identify the requested NFTs, and provide the requested NFTs if the necessary conditions are met by the requesting user 208. If the NFT manager 232 determines that there is not an available NFT or the requesting user 208 has not met the necessary conditions, then the NFT manager 232 may output an indication that the requested NFT cannot be provided.

In the case of the NFT manger 232 providing the requested NFT, the NFT manager 232 may store data indicating the parties of the transaction in the distributed leger 254. The data may indicate the previous user who owned the NFT, the requesting user, and data to identify the NFT itself. The NFT manager 232 may also provide a notification 266 to the computing device 210 of the requesting user 208 indicating that the requesting user 208 now has the requested NFT 280.

In the example of FIG. 2 and in stage B, the user 208 may use the computing device 210 to identify chemical signature 256. The user 208 may identify the chemical signature 256 by using various search queries. The user 208 may wish to utilize the chemical signature 256 to make various products. The user 208 may request the right to use the chemical signature 256 through the computing device 210. The computing device 210 may provide the request 268 to the server 206. The request 268 may indicate a request for an NFT of the chemical signature 256. The NFT manager 232 may receive the request 268 and determine whether there are any NFTs that match the request. The NFT manager 232 may access the distributed ledger 254 to identify the NFTs of the chemical signature 256. The NFT manager 232 may identify the NFT 280. The NFT 280 may indicate that the owner is the user 202. The NFT 280 may indicate the conditions under which the NFT manager 232 can transfer the NFT 280 to another user. One of those conditions may be, for example, to pay a fee. In this case, the requesting user 208 may pay the requested fee. The NFT manager 232 may provide data to the distributed ledger 232 indicating the transfer of the NFT 280 from the user 202 to the requesting user 208. The NFT manager 232 may also generate a notification 266 indicating the transfer of the NFT 280 to the requesting user 208. The NFT manager 232 may provide the notification 266 to the computing device 210 of the requesting user 208.

The server 106 may provide users the ability to modify existing chemical signatures. In this case, a modifying user 212 may identify a chemical signature 256 to modify. The modifying user 212 may use the computing device 214 to identify a chemical signature 256 to modify. The computing device 214 may be a desktop computer, laptop computer, mobile phone, smart watch, wearable device, and/or any other type of device that is configured to communicate with other devices. The modifying user 212 may use various search queries to identify the chemical signature 256 similar to the user 208. The modifying user 212 may provide the formula 274 for the modification 272 to the chemical signature 256 to the server 206. This process may be similar to the user 202 providing the chemical signature 256 of the formula 258. In this way, the computing device 214 may provide the modification 272 to the chemical signature 256 with the formula 274 and the user identifier 276 for the user 212.

The server 206 may receive the modification 272 to the chemical signature 256 and the user identifier 276. The NFT minter 224 may determine that the modification 272 to the chemical signature 256 is a modification 272 to the chemical signature 256. The NFT minter 224 may mint NFTs for the modified chemical signature 272 that indicates that the modifying user 212 and/or the originating user 202 are permitted to use the modified chemical signature 272. Some NFTs may permit the modifying user 212 to use the modified chemical signature 272. Some NFTs may permit the originating user 202 to use the modified chemical signature 272. Some NFTs may permit the modifying user 212 and the originating user 202 to use the modified chemical signature 272.

The NFT minter 224 may mint a limited number of number of NFTs for the modified chemical signature 272. The number of minted NFTs may be based on various rules that utilize factors similar to those used by the attribution rules 126 of FIG. 1 related to the modified chemical signature 178. The server 206 may store the NFTs in the distributed ledger 254. The distributed ledger 254 may use blockchain technology and may be accessible through a network 252. As an example, the NFT minter 224 may mint an NFT 286 based on the modified chemical signature 272. The NFT 286 may indicate that the user 202 and the user 212 have a right to use the modified chemical signature 272. The NFT minter 224 may store the NFT 286 and other NFTs in the distributed ledger 254.

In the example of stage C and in FIG. 2, the modifying user 212 may use the computing device 214 to communicate with the server 206. The modifying user 212 may identify the chemical signature 256 as one that the modifying user 212 wishes to modify. The modifying user 212 may identify the chemical signature 256 by using a search query, browsing a list of chemical signatures, following recommendations of other users, and/or any other similar search technique. The modifying user 212 may view the chemical signature 256 and modify it by adding three grams of the chemical 257.

The computing device 212 may provide the modified chemical signature 272 of the chemical signature 156 to the server 206. The computing device 212 may also provide the formula 274 that includes the formula of the modified chemical signature 272, which is two grams of chemical 217, three grams of chemical 233, five grams of chemical 249, and three grams of chemical 257. The computing device 212 may also provide the user identifier 276 of the user 212. The server 206 may store the modified chemical signature 272 in the chemical signatures storage 222.

The NFT minter 224 may determine to mint three NFTs based on the modified chemical signature 272. The NFT minter 224 may determine to mint three NFTs based on various rules, such as the NFT minter 224 should mint three NFTs for a chemical signature that is modified by a user who has not yet provided or modified a chemical signature. The NFT minter 224 may store the three NFTs, NFT 286, 288, and 290 in the distributed ledger 254. Initially, each of the NFTs 286, 288, and 290 may indicate that the user 202, the user 212, and/or the user 202 and user 212 have the right to use the modified chemical signature 272.

In some implementations, the server 206 may include a usage monitor 228. The usage monitor 228 may be implemented by one or more processors included in the server 206. The processors may execute code stored in a storage device included in and/or accessible by the server 206. The usage monitor 228 may be configured to monitor the usage of the NFTs minted by the NFT minter 224. These NFTs may include NFTs for original chemical signatures such as NFTs 278, 280, 282, and 284 and NFTs for modified chemical signatures such as NFTs 286, 288, and 290. The usage monitor 228 may monitor the usage of the NFT by monitoring access to the distributed ledger 254 and/or the chemical signatures 222. The usage monitor 228 may store usage data in the indicia of use 226. The indicia of use 226 may be located in a storage device that is included in or accessible by the server 206.

The usage data that the usage monitor 228 stored in the indicia of use 226 may include a user identifier, data identifying the chemical signature, data identifying the NFT, a date and time of the usage or access, and/or any other similar usage data. The usage data may indicate attempted uses by uses who may not be owners of an NFT for the corresponding chemical signature. This data may include a user identifier, data identifying the chemical signature, data identifying one or more NFTs of the chemical signature, a date and time of the attempted usage or access, and/or any other similar usage data. The usage data may also include a counter that indicates the number of uses or accesses and/or the attempted uses or accesses. In some implementations, the NFT minter 224 may use the indicia of use 226 as one or more of the factors to determine a number of NFTs to mint.

In some implementations, the server 206 may include a usage report generator 230. The usage report generator 230 may be implemented by one or more processors included in the server 206. The processors may execute code stored in a storage device included in and/or accessible by the server 206. The usage report generator 230 may be configured to generate usage reports for the NFTs based on the indicia of use 226. The usage report generator 230 may be configured to generate usage reports specific to a user, chemical signature, NFT, date or time, and/or any other similar data stored in the indicia of use 226. The usage report generator 230 may generate reports in response to a query from a user. For example, a user may request a report that indicates the usage of NFT 278 and the NFTs related to chemical signatures that a modified from the chemical signature 256 of the NFT 278. Another user may request a report of the NFTs used on Jan. 25, 2022.

In some implementations, the usage monitor 228 may be configured to predict the interest of a new chemical signature. The usage monitor 228 may make this prediction based on the indicia of use 226 and the chemical signatures 222. The usage monitor 228 may use pattern recognition to determine characteristics of frequently and less frequently used chemical signatures. In some implementations, the NFT minter 224 may use the characteristics of frequently and less frequently used chemical signatures to determine a number of NFTs to mint for a new or modified chemical signature. In some implementations, the characteristics of frequently and less frequently used chemical signatures may be used to determine a fee for an NFT, chemical signature, and/or an attribution value for the originating user and/or modifying user.

In some implementations, the usage monitor 228 may use machine learning to train a model that is configured to predict the interest in a new chemical signature. In this case, the usage monitor 228 may train a model using the indicia of use 226. This model may be configured to receive a new chemical signature and predict a number of users and/or a number of requests that the server 206 may receive for the chemical signature. The NFT minter 224 may use these models to determine the number of NFTs to mint for a new or modified chemical signature.

Figure 3:
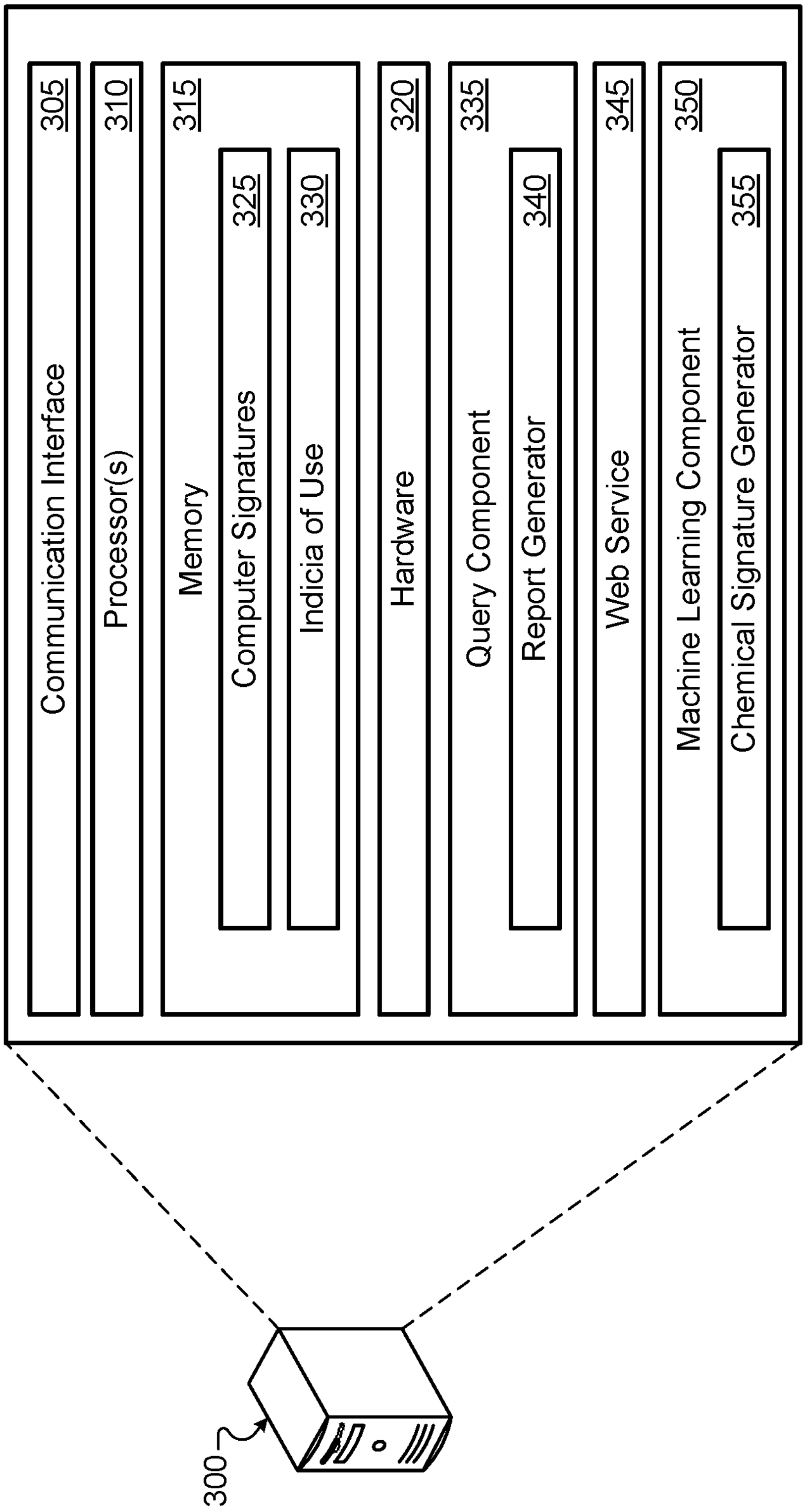
FIG. 3 is an example server that is configured recommend a chemical signature based on user interest.

FIG. 3 is an example server 300 that is configured recommend a chemical signature based on user interest. The server 300 may be any type of computing device that is configured to communicate with other computing devices. The server 300 may communicate with other computing devices using a wide area network, a local area network, the internet, a wired connection, a wireless connection, and/or any other type of network or connection. The wireless connections may include Wi-Fi, short-range radio, infrared, and/or any other wireless connection. The server 300 may be similar to the server 106 of FIG. 1 and or the server 206 of FIG. 2. Some of the components of the server 300 may be implemented in a single computing device or distributed over multiple computing devices. Some of the components may be in the form of virtual machines or software containers that are hosted in a cloud in communication with disaggregated storage devices.

The server 300 may include a communication interface 305, one or more processors 310, memory 315, and hardware 320. The communication interface 305 may include communication components that enable the server 300 to transmit data and receive data from other devices and networks. In some implementations, the communication interface 305 may be configured to communicate over a wide area network, a local area network, the internet, a wired connection, a wireless connection, and/or any other type of network or connection. The wireless connections may include Wi-Fi, short-range radio, infrared, and/or any other wireless connection.

The hardware 320 may include additional user interface, data communication, or data storage hardware. For example, the user interfaces may include a data output device (e.g., visual display, audio speakers), and one or more data input devices. The data input devices may include, but are not limited to, combinations of one or more of keypads, keyboards, mouse devices, touch screens that accept gestures, microphones, voice or speech recognition devices, and any other suitable devices.

The memory 315 may be implemented using computer-readable media, such as computer storage media. Computer-readable media includes, at least, two types of computer-readable media, namely computer storage media and communications media. Computer storage media includes volatile and non-volatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD), high-definition multimedia/data storage disks, or other optical storage, magnetic cassettes, magnetic tape, magnetic disk storage or other magnetic storage devices, or any other non-transmission medium that can be used to store information for access by a computing device. In contrast, communication media may embody computer-readable instructions, data structures, program modules, or other data in a modulated data signal, such as a carrier wave, or other transmission mechanism.

The memory 315 may store computer signatures 325. The computer signatures 325 may include chemical signatures similar to those described above. In this case, the computer signatures may be similar to the chemical signatures 122 of FIG. 1 and/or the chemical signatures 222 of FIG. 2. The computer signatures 325 may also include any other kind of digital signature that may uniquely identify an object and/or idea. The computer signatures 325 may include data identifying originating users who created the computer signatures, a modifying user who may have modified the computer signatures, a date and time of the creation or modification, and related computer signatures, such as those that are modified versions of other computer signatures. The computer signatures 325 may include data related to the NFTs that may correspond to the computer signatures, attribution values for each of the computer signatures, and/or any other similar data.

The memory 315 may store indicia of use 330. The indicia of use 330 may be similar to the indicia of use 226 of FIG. 2. The indicia of use 330 may store data related to the usage of the computer signatures 325. The usage data may include the date and time that a computer signature was accessed, used, and/or transferred, data identifying the accessing user, data identifying any funds exchanged between users as part of the usage, access, and/or transfer. Some of the usage data may also be included in the NFTs.

The one or more processors 310 may implement a web service 345. The web service 345 may be configured to receive verification requests for issued NFTs that may be associated with the computer signatures included the computer signatures. In the case where the web service 345 successfully verifies requests for issued NFTs, the web service 345 may store data in the indicia of use 330 indicating the NFT, the verification, data identifying a requesting user, a timestamp, and/or any other similar data. The web service 345 may be accessed by a computing device that is communicating with the server 300 such as a mobile phone.

The one or more processors 310 may implement a machine learning component 350. The machine learning component 350 may be configured to read the indicia of use 330 and train a model using machine learning and the indicia of use 330. The model may be configured to generate a new chemical signature. The chemical signature generator 355 may utilize the model to generate the new chemical signature. The model may be configured to receive data indicating a target number of accesses, uses, users, and/or any other similar target for a new chemical signature and output a new chemical signature. The chemical signature generator 355 may use the model to process requests from users and/or to automatically generate new chemical signatures that target a range of accesses, uses, users, and/or any other similar target.

The one or more processors 310 may implement a query component 335. The query component 335 may be configured to receive queries directed to the data in the indicia of use 330. The query component 335 may include a report generator 340 that is configured to generate reports based on those queries. The query component 335 may be configured to analyze the indicia of use 330 for data that is responsive to the query. The query component 335 may provide that data to the report generator 340 for generation of the report. The report generator 340 may output the report to the device that provided the query.

Figure 4:
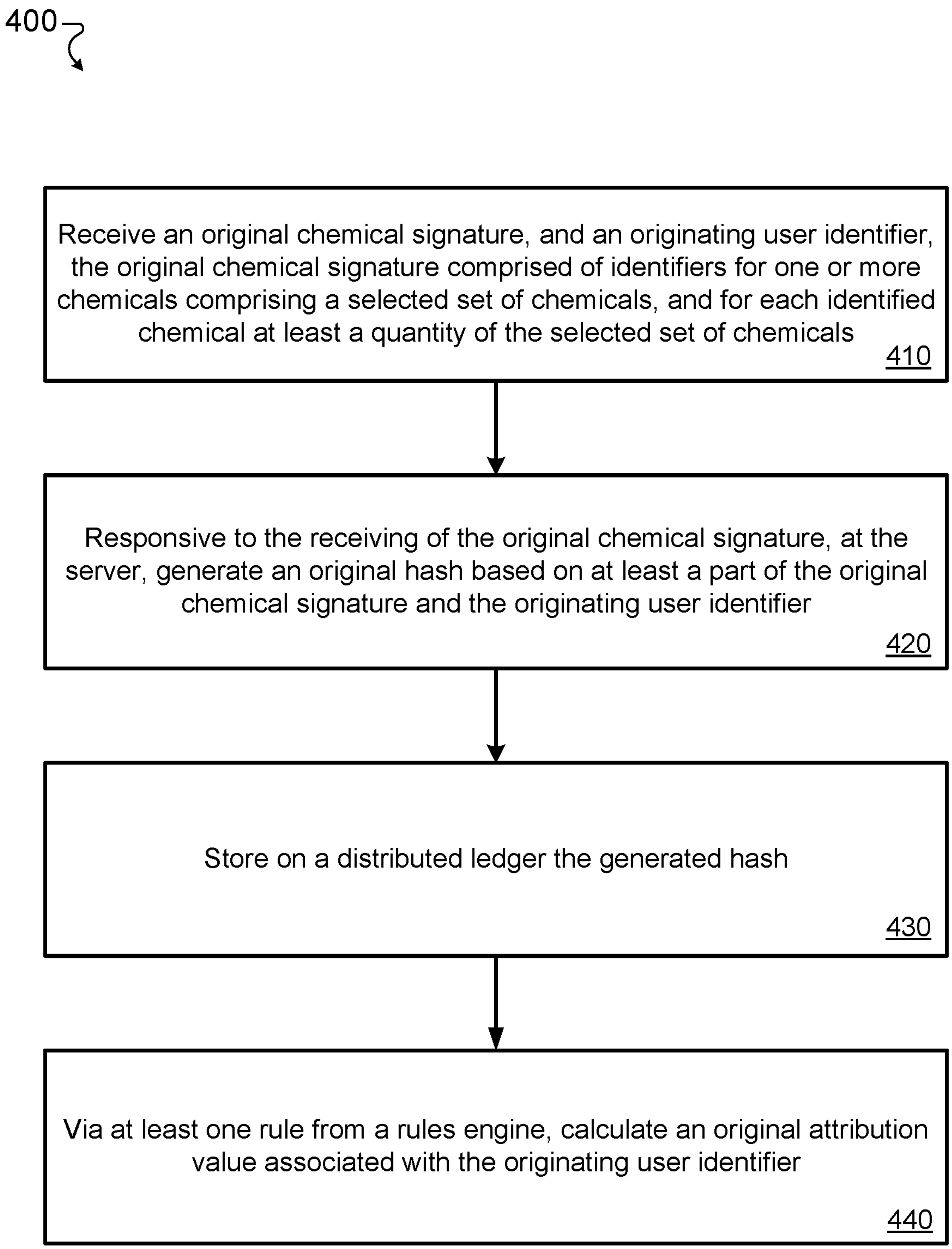
FIG. 4 is a flowchart of an example process for managing chemical signatures and determining compensation for creators of those chemical signatures.

FIG. 4 is a flowchart of an example process 400 for managing chemical signatures and determining compensation for creators of those chemical signatures. In general, the process 400 receives a chemical signature and a user identifier of a user who created the chemical signature. The process 400 generates a hash of the chemical signature and the user identifier and stores the hash in a distributed ledger. The process 400 determines an attribution value to assign to the chemical signature that indicates compensation to provide to the user when others request the chemical signature. The process 400 will be described as being performed by the server 106 of FIG. 1 and will include references to components of the FIG. 1. In some implementations, the process 400 may be performed by the server 206 of FIG. 2 and/or the server 300 of FIG. 3.

The server 106 receives an original chemical signature, and an originating user identifier, the original chemical signature comprised of identifiers for one or more chemicals comprising a selected set of chemicals, and for each identified chemical at least a quantity of the selected set of chemicals (410). In some implementations, the server 106 receives the original chemical signature and originating user identifier from a computing device of the originating user.

Responsive to the receiving of the original chemical signature, the server 106 generates an original hash based on at least a part of the original chemical signature and the originating user identifier (420). The server 106 stores, on a distributed ledger, the generated hash (430). In some implementations, the distributed ledger may be a blockchain. In some implementations, the server 106 may mint an NFT based on the original chemical signature and the originating user identifier. The server 106 may store the NFT in the distributed ledger.

Via at least one rule from a rules engine, the server 106 calculates an original attribution value associated with the originating user identifier (440). The attribution value may indicate a portion of a payment received from a requesting user that the server 106 should provide to the originating user when the requesting user requests access to or use of the original chemical signature. In some implementations, the rules of the rules engine may be included in a smart contract that is located in the distributed ledger. In some implementations, the server 106 receives a request for the original chemical signature from a requesting user. The request may include a payment. The server 106 may deposit at least a port of the receive payment in an account of the originating user according to the rules in the rules engine and/or the attribution value for the original chemical signature.

In some implementations, the server 106 may receive a modification to the original chemical signature. The modification may include a modifying user identifier of the user modifying the original chemical signature. In response to receiving the modification, the server 106 may retrieve the original chemical signature and/or the originating user identifier. The server 106 generates the modified chemical signature based on the original chemical signature and the received modification. The server 106 stores the modified chemical signature.

The server 106 generates two new hashes. The first hash is based on the modified chemical signature and the originating user identifier. This first hash may be related to the originating user. The second hash is based on the modified chemical signature and the modifying user identifier. This second hash may be related to the modifying user. The server 106 stores these two hashes in the distributed ledger. The server 106 generates new attribution values based on the rules in the rules engine. The first attribution value is for the originating user and the modified chemical signature. The second attribution value is for the modifying user and the modified chemical signature.

In some implementations, the server 106 receives a request for the modified chemical signature from a requesting user. The request may also include a payment. The server 106 may divide the payment according to the attribution rule for the originating user and the attribution rule for the modifying user and deposit those two amounts in the respective accounts of the originating user and modifying user.

In some implementations, the server 106 may mint a new NFT based on the modified chemical signature and the originating user identifier and another NFT based on the based on the modified chemical signature and the modifying user identifier. In some implementations, the server 106 may mint a single composite NFT based on the modified chemical signature. In response to receiving a request for the modified chemical signature, the server 106 may serve the single composite NFT to the requesting user. In some implementations, this serving may include collecting a payment from the requesting user and providing portions of that payment to the originating user and the modifying user according to the respective attribution values.

In some implementations, the server 106 mints a first NFT based on the first has and a second NFT based on the second hash. In response to receiving the request for the modified chemical signature, the server 106 provides a portion of the payment received from the requesting user to the originating user, and the server 106 serves the first NFT. The server 106 may serve the first NFT to the requesting user. The server 106 provides a portion of the payment to the modifying user, and the server 106 may service the second NFT. The server 106 may serve the second NFT to the requesting user. In some instances, the server 106 does not serve the second NFT to the requesting user.

Figure 5:
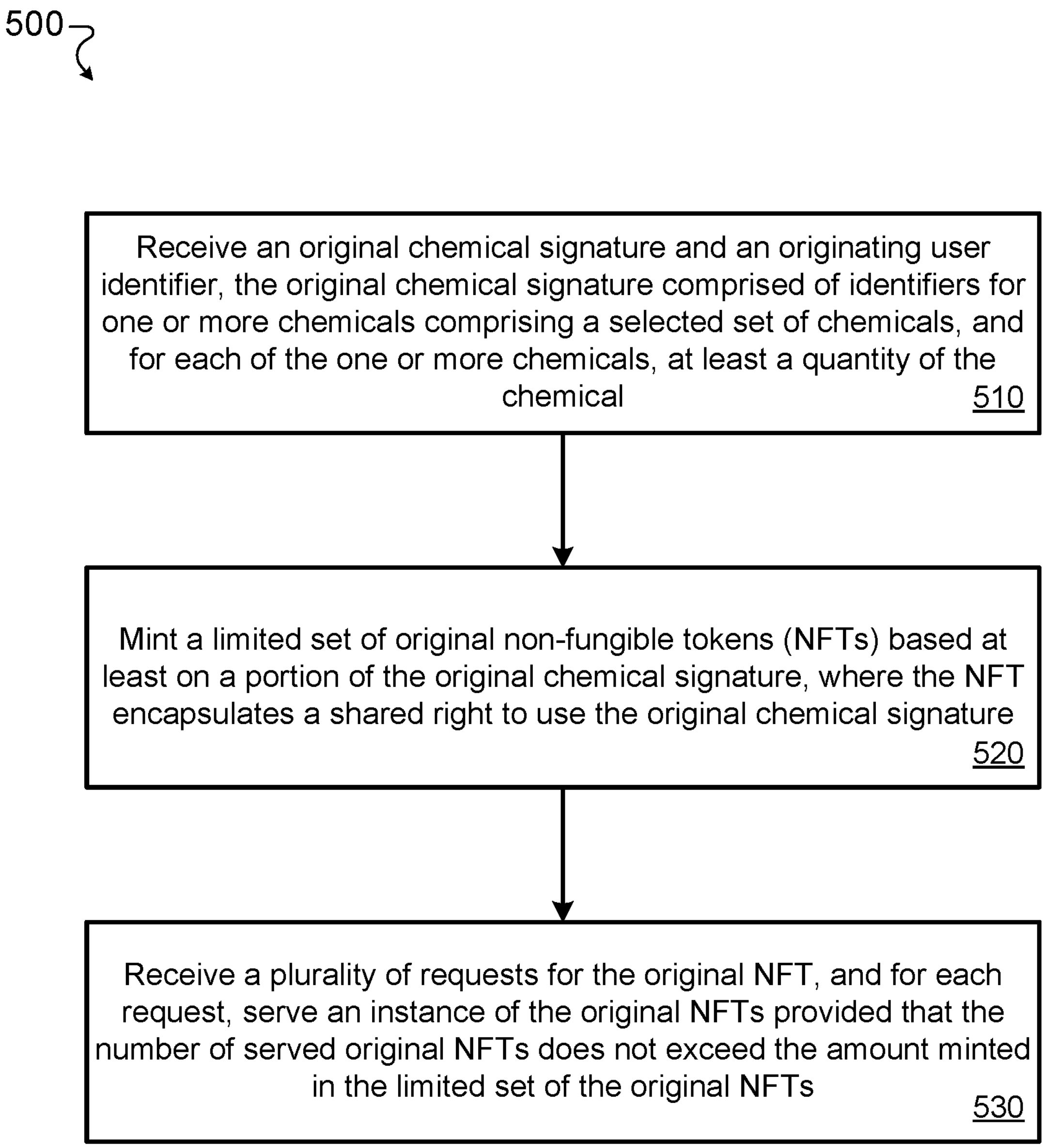
FIG. 5 is a flowchart of an example process for managing usage of chemical signatures using non-fungible tokens.

FIG. 5 is a flowchart of an example process 500 for managing usage of chemical signatures using non-fungible tokens. In general, the process 500 receives a chemical signature and a user identifier of a user who created the chemical signature. The process 500 mints one or more NFTs based on the chemical signature and a user identifier. The process 500 provides one of the NFTs to a user requesting access to or the right to use the chemical signature. The process 500 will be described as being performed by the server 206 of FIG. 2 and will include references to components of the FIG. 2. In some implementations, the process 500 may be performed by the server 106 of FIG. 1 and/or the server 300 of FIG. 3.

The server 206 receives an original chemical signature and an originating user identifier, the original chemical signature comprised of identifiers for one or more chemicals comprising a selected set of chemicals, and for each of the one or more chemicals, at least a quantity of the chemical (510). In some implementations, the server 106 receives the original chemical signature and originating user identifier from a computing device of the originating user.

The server 206 mints a limited set of original non-fungible tokens (NFTs) based at least on a portion of the original chemical signature, where the NFT encapsulates a shared right to use the original chemical signature (520). In some implementations, the NFT initially provides the originating user the shared right to use the original chemical signature.

The server 206 receives a plurality of requests for the original NFT, and for each request, serves an instance of the original NFTs provided that the number of served original NFTs does not exceed the amount minted in the limited set of the original NFTs (530). In some implementations, the server 106 monitors for usage of at least one of the original NFTs. The server 160 may store indicia of that usage and generate a report based on that indicia of usage. In some implementations, the server 106 determines a probability of interest in a new chemical signature based on the indicia of usage. In some implementations, the server 106 may train a model using machine learning and the indicia of usage as training data. The model may be configured to determine the probability of interest in a new chemical signature.

In some implementations, the server 106 receives a modification to the original chemical and a modifying user identifier of the modifying user. The server 106 mints a limited number of modifying NFTs that encapsulate a shared right to use the modified chemical signature if the user also has the right to use the original chemical signature. The server 106 receives a plurality of requests for the modifying NFTs. The server 106 may serve one of the modifying NFTs in response to each request provided the server 106 does not exceed the number of minted modifying NFTs.

In some implementations, the server 106 monitors for usage of the original NFT and/or the modifying NFT. The server 106 stores indicia of the usage of the original NFT and/or the modifying NFT. The server 106 may generate a report based on the indicia of usage of the original NFT and/or the indicia of usage of the modifying NFT. In some implementations, the server 106 determines a probability of interest in a new chemical signature based on the indicia of usage of the original NFT and/or the modifying NFT. In some implementations, the server 106 may train a model using machine learning and the indicia of usage of the original NFT and/or the modifying NFT as training data. The model may be configured to determine the probability of interest in a new chemical signature and/or a modification to an existing chemical signature.

The components and features of the system 100, system 200, server 300, process 400, and process 500 may be combined in any manner. For example, the NFT manager 232 may be integrated into the server 106 to provide additional functionality for the system 100. The attribution value generator 128 may be integrated into the server 206.

Although a few implementations have been described in detail above, other modifications are possible. In addition, the logic flows depicted in the figures do not require the particular order shown, or sequential order, to achieve desirable results. In addition, other actions may be provided, or actions may be eliminated, from the described flows, and other components may be added to, or removed from, the described systems. Accordingly, other implementations are within the scope of the following claims.

What is claimed is:

1. A method to track user interest in chemical signatures comprising:

receiving, at a server, an original chemical signature and an originating user identifier, the original chemical signature comprising information associated with chemicals for inhalants or combustibles in a format that can be interpreted by a printing apparatus to print the chemicals in pre-vapor formulations in a substrate based on the original chemical signature, the original chemical signature further comprising identifiers for one or more chemicals comprising a selected set of chemicals, and for each of the one or more chemicals, at least a quantity of the chemical;

minting a limited set of original non-fungible tokens (NFTs) based at least on a portion of the original chemical signature, wherein the NFT encapsulates a shared right to use the original chemical signature for printing the chemicals onto the substrate; and receiving a plurality of purchase requests for the original NFT, and for each request, serving an instance of the original NFTs provided that the number of served original NFTs does not exceed the amount minted in the limited set of the original NFTs.

2. The method of claim 1, further comprising:

responsive to the receiving of the original chemical signature, at the server, generating an original hash based on at least a part of the original chemical signature and the originating user identifier;

storing on a distributed ledger the generated hash; and via at least one rule from a rules engine, calculating an original attribution value associated with the originating user identifier.

3. The method of claim 2, comprising:

receiving, at the server, a request for the original chemical signature and a payment for the original chemical signature from a requesting user; and responsive to receiving the request, via at least one rule from the rules engine and based at least on the original attribution value, depositing at least a portion of the payment in an account associated with the originating user identifier.

4. The method of claim 2, wherein storing on the distributed ledger comprises minting the non-fungible token (NFT).

5. The method of claim 2, comprising:

receiving, at the server, a modification to the original chemical signature and a modifying user identifier;

responsive to receiving the modification to the original chemical signature and the modifying user identifier, retrieving, at the server, the original chemical signature and the originating user identifier;

generating a modified chemical signature based at least on the original chemical signature and the modification to the original chemical signature;

storing the modified chemical signature;

generating a first new hash associated with the originating user identifier based on at least a part of the modified chemical signature and the originating user identifier, and generating a second new hash associated with the modifying user identifier based on at least a part of the modified chemical signature and the modifying user identifier storing on the distributed ledger the first new hash and the second new hash; and based on the at least one rule from a rules engine, calculating a new first attribution value associated with the originating user identifier and calculating a new second attribution value associated with the modifying user identifier.

6. The method of claim 5, wherein the at least one rule from a rules engine is a smart contract.

7. The method of claim 5, comprising:

receiving at the server a request for the modified chemical signature and a payment for the modified chemical signature from a requesting user; and responsive to receiving the request, via at least one rule from the rules engine and based at least on the original attribution value, depositing at least a first portion of the payment in an account associated with the originating user identifier and at least a second portion of the payment in an account associated with the modifying user identifier.

8. The method of claim 5, wherein the storing of at least one of the first new hash and the second new hash comprises minting the non-fungible token (NFT).

9. The method of claim 5, comprising:

via at least one rule from the rule engine, minting a single composite NFT, responsive to receiving the request, via at least one rule from the rules engine and based at least on the original attribution value, depositing at least a first portion of a payment in an account associated with the originating user identifier and at least a second portion of the payment in an account associated with the modifying user identifier and serving the single composite NFT.

10. The method of claim 4, comprising:

via at least one rule from the rule engine, minting a first NFT based at least on the first hash and minting a second NFT based at least on the second hash;

responsive to receiving the request, via at least one rule from the rules engine and based at least on the first attribution value, depositing at least a first portion of the received payment in an account associated with the originating user identifier and serving the first NFT; and responsive to receiving the request, via the at least one rule from the rules engine, and based at least on the second attribution value, depositing at least a second portion of the received payment in an account associated with the modifying user identifier.

11. The method of claim 1, comprising:

monitoring at the server for indicia of transactional use of the original NFT;

storing the indicia of transactional use; and generating reports of transactions based at least on some of the stored indicia of use.

12. The method of claim 11, comprising:

based on volume of transactions reflected in the stored indicia of transactional use, determining a probability of interest in a new chemical signature.

13. The method of claim 12, wherein determining the probability of interest is via a machine learning software component.

14. The method of claim 1, wherein the shared right encapsulated by the original NFT is a right to use the original chemical signature in combination with modifications, but not alone; and comprising:

receiving, at the server, a modification to the original chemical signature and a modifying user identifier;

minting a limited set of modifying NFTs based at least on a portion of the received modification, wherein the modifying NFT encapsulates a shared right to use the modification of the chemical signature in combination if there is also a right to use the original chemical signature in combination, and receiving a plurality of requests for the modifying NFT, and for each request, serving an instance of the modifying NFTs provided that the number of served modifying NFTs does not exceed the amount minted in the limited set of modifying NFTs.

15. The method of claim 14, comprising:

monitoring, at the server, for indicia of transactional use of the original NFT;

storing the indicia of transactional use of the original NFT;

monitoring at the server for indicia of transactional use of the modifying NFT;

storing the indicia of transactional use of the modifying NFT; and generating reports of transactions based at least on some of the stored indicia of transactional use of the original NFT and at least some of the stored indicia of transactional use of the modifying non-fungible token.

16. The method of claim 15, comprising:

based on volume of transactions reflected in the stored indicia of transactional use of the original NFT and the stored indicia of transactional use of the modifying NFT, determining a probability of interest in a new chemical signature.

17. The method of claim 16, wherein determining the probability of interest is via a machine learning software component.

18. A method to track user interest in chemical signatures comprising:

receiving, at a server, an original chemical signature and an originating user identifier, wherein the original chemical signature comprises:

identifiers for *cannabis*, cannabidiol, terpenes, or combinations thereof; and for each identified chemical, at least a quantity of the chemical, wherein the identified chemicals are for combination with a smokable substrate;

communicating data from the original chemical signature to a printing device configured to inject the identified chemicals at the specified quantities into the smokable substrate;

minting a limited set of original non-fungible tokens (NFTs) based at least on a portion of the original chemical signature, wherein the NFT encapsulates a shared right to direct the printing device to inject chemicals based on the original chemical signature; and receiving a plurality of purchase requests for the original NFT, and for each request, serving an instance of the original NFTs provided that the number of served original NFTs does not exceed the amount minted in the limited set of the original NFTs.

19. A method to track user interest in chemical signatures comprising:

receiving, at a server, an original chemical signature and an originating user identifier, the original chemical signature specifying one or more chemicals that can be applied to a smokable substrate and respective quantities for applying to the smokable substrate;

transmitting the original chemical signature to an apparatus, wherein the apparatus is configured to apply the one or more chemicals to the smokable substrate based on the original chemical signature;

minting a limited set of original non-fungible tokens (NFTs) based at least on a portion of the original chemical signature, wherein the NFT encapsulates a shared right to use the original chemical signature; and receiving a plurality of purchase requests for the original NFT, and for each request, serving an instance of the original NFTs provided that the number of served original NFTs does not exceed the amount minted in the limited set of the original NFTs.

20. The method of claim 19, comprising:

monitoring, at the server, for indicia of use of the original NFT;

storing the indicia of use of the original NFT;

generating reports based at least on some of the stored indicia of use of the original NFT and at least some of the stored indicia of use of the NFT;

based on the stored indicia of use of the original NFT, determining a probability of interest in a new chemical signature, wherein determining the probability of interest is via a machine learning software component.

* * * * *